United States Patent [19]

Baschang et al.

[11] Patent Number: 4,885,285
[45] Date of Patent: Dec. 5, 1989

[54] PHOSPHORUS COMPOUNDS, PROCESSES FOR THEIR MANUFACTURE, AND THEIR USE

[75] Inventors: Gerhard Baschang, Bettingen, Switzerland; Albert Hartmann, Grenzach, Fed. Rep. of Germany; Hans Hirt, Allschwil, Switzerland; Bohumir Lucas, Basel, Switzerland; Peter Wirz, Münchenstein, Switzerland

[73] Assignee: Ciba-Geigy Corporation, Ardsley, N.Y.

[21] Appl. No.: 773,707

[22] Filed: Sep. 9, 1985

[30] Foreign Application Priority Data

Sep. 13, 1984 [CH] Switzerland ................. 4378/84

[51] Int. Cl.$^4$ ................................ A61K 31/66
[52] U.S. Cl. ........................... 514/114; 260/403
[58] Field of Search .......................... 514/114

[56] References Cited

U.S. PATENT DOCUMENTS

| | | | |
|---|---|---|---|
| 2,436,699 | 2/1948 | Rose | 260/403 |
| 2,447,715 | 8/1948 | Rose | 260/326 |
| 3,663,235 | 5/1972 | Menz et al. | 99/123 |
| 4,119,714 | 10/1978 | Kny et al. | 514/78 |
| 4,254,115 | 3/1981 | Davidson et al. | 424/211 |
| 4,323,560 | 4/1982 | Baschang et al. | 424/177 |
| 4,406,890 | 9/1983 | Tarcsay et al. | 424/177 |
| 4,414,204 | 11/1983 | Tarcsay et al. | 424/177 |
| 4,423,038 | 12/1983 | Baschang et al. | 424/177 |
| 4,493,832 | 1/1985 | Teraji et al. | 424/199 |
| 4,534,899 | 8/1985 | Sears | 260/403 |
| 4,548,923 | 8/1985 | Sears | 260/403 |
| 4,666,893 | 5/1987 | Tsuchiya | 514/78 |
| 4,742,051 | 5/1988 | Muirhead et al. | 514/114 |

FOREIGN PATENT DOCUMENTS

| | | | |
|---|---|---|---|
| 72111 | 2/1983 | European Pat. Off. | 514/114 |
| 72286 | 2/1983 | European Pat. Off. | 514/114 |
| 1530138 | 10/1978 | United Kingdom | 514/114 |

OTHER PUBLICATIONS

Derwent Abstract of European Application No. 138,558.
Derwent Abstract of Japanese Application No. 52087221.
Translation of European Application No. 102,319, Published 3-7-84.

Primary Examiner—James H. Reamer
Attorney, Agent, or Firm—Irving M. Fishman; JoAnn Villamizar

[57] ABSTRACT

Cephalin derivatives of the formula I

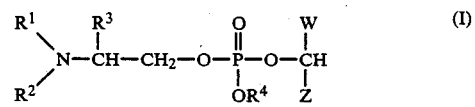

in which $R^1$ and $R^2$ each represents, independently of the other, hydrogen or lower alkyl, $R^3$ represents hydrogen, lower alkoxycarbonyl, carbamoyl or free or protected carboxy, $R^4$ represents hydrogen or an aliphatic, aromatic, aromatic-aliphatic or cycloaliphatic radical, W represents hydrogen and Z represents a 1,2-dihydroxyethyl, 2-hydroxyethyl or hydroxymethyl group in which at least one hydroxy group is esterified by an aliphatic $C_{6-30}$-carboxylic acid or etherified by an aliphatic $C_{6-30}$-alcohol and in which the other hydroxy group, if present, is free, esterified by an aliphatic $C_{2-30}$-carboxylic acid or etherified by an aliphatic $C_{1-30}$-alcohol, or W represents hydroxymethyl or a hydroxymethyl group that is esterified by an aliphatic $C_{6-30}$-alcohol and Z represents a hydroxymethyl group that is esterified by an aliphatic $C_{6-30}$-carboxylic acid or etherified by an aliphatic $C_{6-30}$-alcohol, and their salts are suitable for the prophylaxis and treatment of virus infections in warm-blooded animals.

11 Claims, No Drawings

PHOSPHORUS COMPOUNDS, PROCESSES FOR THEIR MANUFACTURE, AND THEIR USE

The invention relates to the use of cephalin derivatives of the formula I

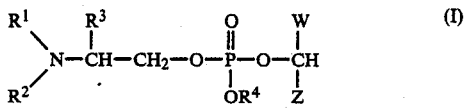

in which $R^1$ and $R^2$ each represents, independently of the other, hydrogen or lower alkyl, $R^3$ represents hydrogen, lower alkoxycarbonyl, carbamoyl or free or protected carboxy, $R^4$ represents hydrogen or an aliphatic, aromatic, aromatic-aliphatic or cycloaliphatic radical, W represents hydrogen and Z represents a 1,2-dihydroxyethyl, 2-hydroxyethyl or hydroxymethyl group in which at least one hydroxy group is esterified by an aliphatic $C_{6-30}$-carboxylic acid or etherified by an aliphatic $C_{6-30}$-alcohol and in which the other hydroxy group, if present, is free, esterified by an aliphatic $C_{2-30}$-carboxylic acid or etherified by an aliphatic $C_{1-30}$-alcohol, or W represents hydroxymethyl or a hydroxymethyl group that is esterified by an aliphatic $C_{6-30}$-carboxylic acid or etherified by an aliphatic $C_{6-30}$-alcohol and Z represents a hydroxymethyl group that is esterified by an aliphatic $C_{6-30}$-carboxylic acid or etherified by an aliphatic $C_{6-30}$-alcohol, and to the use of salts of these compounds, for the prophylaxis and treatment of virus infections in warm-blooded animals, including human beings, and for the manufacture of pharmaceutical preparations for use in the prophylaxis and treatment of virus infections in warm-blooded animals, including human beings, or as intermediates for the manufacture of compounds of the formula I that are suitable for the prophylaxis and treatment of virus infections.

The invention also relates to a method for the prophylaxis and treatment of virus infections in warm-blooded animals, including human beings, characterised in that an antivirally active amount of a compound of the formula I or a pharmaceutically acceptable salt thereof is administered.

The invention further relates to novel pharmaceutical preparations that contain as active ingredient, especially as the only active ingredient, such a pharmaceutically acceptable compound of the formula I or a pharmaceutically acceptable salt of such a compound together with a pharmaceutical carrier.

The invention also relates to those compounds of the formula I from the above-mentioned group whose use in a method for the therapeutic treatment of the human or animal body is not part of the prior art, and to pharmaceutically acceptable salts of these compounds for use in a method for the therapeutic treatment of the human or animal body, to pharmaceutical preparations containing these compounds and to processes for their manufacture.

The invention relates further to the novel compounds of the formula I and salts of these compounds, to pharmaceutical preparations containing such a compound or such a salt as active ingredient, to their use as medicaments and to processes for the manufacture of these compounds and their salts.

Lower alkyl $R^1$ and $R^2$ is especially methyl or ethyl.

Lower alkoxycarbonyl $R^3$ is especially methoxycarbonyl or ethoxycarbonyl.

Protected carboxy $R^3$ is carboxy protected by a carboxy-protecting group.

Protecting groups and the manner in which they are introduced and removed are described, for example, in "Protective Groups in Organic Chemistry", Plenum Press, London, New York 1973, and in "Methoden der organischen Chemie", Houben-Weyl, 4th Edition, Vol. 15/1, Georg-Thieme-Verlag, Stuttgart 1974 and in Theodora W. Greene, "Protective Groups in Organic Synthesis", John Wiley & Sons, New York 1981. It is characteristic of protecting groups that they can be readily removed, that is to say without undesired secondary reactions taking place, for example by solvolysis, reduction, photolysis or alternatively under physiological conditions.

Carboxy groups are customarily protected in esterified form, such ester groupings being readily cleavable under mild conditions. Carboxy groups protected in this manner contain as esterifying groups especially lower alkyl groups that are branched in the 1-position or suitably substituted in the 1- or 2position. Preferred carboxy groups in esterified form are, inter alia, tert.-lower alkoxycarbonyl, for example tert.-butoxycarbonyl, arylmethoxycarbonyl having one or two aryl radicals, these being phenyl radicals optionally mono- or poly-substituted, for example, by lower alkyl, such as tert.-lower alkyl, for example tert.-butyl, lower alkoxy, such as methoxy, hydroxy, halogen, for example chlorine, and/or by nitro, such as benzyloxycarbonyl optionally substituted, for example, as mentioned above, for example 4-methoxybenzyloxycarbonyl or 4-nitrobenzyloxycarbonyl, or diphenylmethoxycarbonyl optionally substituted, for example, as mentioned above, for example diphenylmethoxycarbonyl or di-(4-methoxyphenyl)-methoxycarbonyl, 1-lower alkoxy-lower alkoxycarbonyl, such as methoxymethoxycarbonyl, 1-methoxyethoxycarbonyl or 1-ethoxymethoxycarbonyl, 1-lower alkylthio-lower alkoxycarbonyl, such as 1-methylthiomethoxycarbonyl or 1-ethylthioethoxycarbonyl, aroylmethoxycarbonyl in which the aroyl group represents benzoyl optionally substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which each of the substituents, independently of the others, represents an aliphatic, araliphatic, cycloaliphatic or aromatic hydrocarbon radical that is optionally substituted, for example, by lower alkyl, lower alkoxy, aryl, halogen and/or by nitro, such as corresponding optionally substituted lower alkyl, phenyl-lower alkyl, cycloalkyl or phenyl, for example 2-tri-lower alkylsilylethoxycarbonyl, 2-trimethylsilylethoxycarbonyl or 2-(di-n-butylmethylsilyl)-ethoxycarbonyl, or 2-triarylsilylethoxycarbonyl, such as 2-triphenylsilylethoxycarbonyl.

The organic silyl radicals mentioned hereinbefore and hereinafter preferably contain lower alkyl, especially methyl, as substituent of the silicon atoms. Corresponding silyl groups are especially tri-lower alkylsilyl, especially trimethylsilyl, and also dimethyl-tert.-butylsilyl.

Preferred protected carboxy groups are tert.-lower alkoxycarbonyl, such as tert.-butoxycarbonyl, and especially benzyloxycarbonyl or diphenylmethoxycarbonyl optionally substituted, for example, as mentioned above, such as 4-nitrobenzyloxycarbonyl, and more especially 2-(trimethylsilyl)-ethoxycarbonyl.

An aliphatic, aromatic, aromatic-aliphatic or cycloaliphatic radical $R^4$ is especially a phosphoric acid-protecting group, for example lower alkyl, such as, especially, methyl, optionally substituted phenyl, for example 2-chlorophenyl, or phenyl-lower alkyl that is optionally substituted in the phenyl moiety, such as, especially, benzyl or 4-nitrobenzyl.

A cycloaliphatic radical $R^4$ is especially also cycloalkyl that has 5 or 6 carbon atoms and is unsubstituted or substituted, for example, by lower alkyl, hydroxy or lower alkanoyloxy, such as acetoxy, for example 2,3,4,5,6-pentahydroxycyclohexyl, such as 1-deoxy-myo-inosityl, or 2,3,4,5,6-pentaacetoxycyclohexyl.

An aliphatic $C_{6-30}$-carboxylic acid has preferably an even number of carbon atoms, especially from 12 to 24, more especially from 16 to 24, and very especially from 16 to 22, carbon atoms, is branched or preferably straight-chained and is especially a substituted or preferably unsubstituted alkanoic or alkenoic acid, it being possible for the alkenoic acid to contain from 1 to 3 isolated double bonds, for example a naturally occurring fatty acid, such as, especially, palmitic acid, oleic acid or stearic acid, or also linoleic or linolenic acid. Capric acid, lauric acid, nervonic acid and lignoceric acid may also be mentioned as examples of an aliphatic $C_{6-30}$-carboxylic acid.

An aliphatic $C_{6-30}$-alcohol has preferably an even number of carbon atoms, especially from 12 to 24, more especially from 16 to 24, and very especially from 16 to 22, carbon atoms, is branched or, preferably, straight-chained and is especially a substituted or unsubstituted alkanol or alkenol, there being mentioned as substituents, for example, hydroxy, amino, alkanoylamino or alkenoylamino.

The aliphatic $C_{2-30}$-carboxylic acid mentioned in the definition of the radical Z is especially an optionally substituted alkenoic or, preferably, alkanoic acid, for example acetic acid, propionic acid or butyric acid, or one of the above-mentioned aliphatic $C_{6-30}$-carboxylic acids.

The aliphatic $C_{1-30}$-alcohol mentioned in the definition of the radical Z is especially a substituted or, preferably, unsubstituted alkenol or, preferably, alkanol having up to 30 carbon atoms, for example methanol, ethanol, or one of the above-mentioned aliphatic $C_{6-30}$-alcohols.

The general terms used hereinbefore and hereinafter preferably have the following meanings:

The prefix "lower" denotes radicals having up to and including 7, especially up to and including 4, carbon atoms.

Substituents of phenyl are especially lower alkyl, halogen, lower alkoxy, nitro or lower alkoxycarbonyl.

Lower alkyl is, for example, n-propyl, n-butyl, isobutyl, sec.-butyl, tert.-butyl, also n-pentyl, n-hexyl or n-heptyl, but especially methyl, ethyl or isopropyl.

Halogen is especially chlorine or bromine, also fluorine or iodine.

Lower alkoxy is especially methoxy or ethoxy.

Lower alkoxycarbonyl is especially methoxycarbonyl or ethoxycarbonyl.

The compounds of the formula I in which $R^4$ represents hydrogen or $R^3$ represents carboxy may be in the form of internal salts, that is to say in zwitterionic form, if there is a suitable pH value.

The compounds of the formula I may, for example if they contain more than one basic group, also form acid addition salts with external acids, for example with inorganic acids, such as mineral acids, for example hydrochloric acid, sulphuric acid or phosphoric acid, or with suitable organic carboxylic or sulphonic acids, for example trifluoroacetic, acetic, maleic, fumaric, tartaric, citric, methanesulphonic or 4-toluenesulphonic acid, and also with amino acids, such as arginine and lysine.

The compounds of the formula I may, for example if they contain more acidic than basic groups, for example if $R^4$ represents hydrogen and $R^3$ represents carboxy, form metal or ammonium salts, such as alkali metal and alkaline earth metal salts, for example sodium, potassium, magnesium or calcium salts, and also ammonium salts with ammonia or suitable organic amines, there being suitable for the salt formation especially aliphatic, cycloaliphatic, cycloaliphatic-aliphatic or araliphatic primary, secondary or tertiary mono-, di- or polyamines, and also heterocyclic bases, such as lower alkylamines, for example triethylamine, hydroxy-lower alkylamines, for example 2-hydroxyethylamine, bis-(2-hydroxyethyl)amine, 2-hydroxyethyldiethylamine or tri-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, and bases of the pyridine type, for example pyridine, collidine or quinoline.

For the purpose of isolation or purification it is also possible to use pharmaceutically unacceptable salts. However, only the pharmaceutically acceptable non-toxic salts are used therapeutically and these are therefore preferred.

The novel compounds of the present invention have a number of valuable pharmacological properties.

According to the invention, it has surprisingly been found that the above-mentioned phosphatidyl compounds of the formula I and their pharmaceutically acceptable salts are outstandingly suitable both for the prophylaxis and for the treatment of virus infections as is apparent, for example, from tests on animals as given by way of illustration in the Examples. In these animal tests, animals such as mice or guinea pigs are infected with the most varied types of viruses at a dose that is lethal to all or the great majority of the untreated (control) animals, for example $LD_{80-90}$ and the course of the infection is observed in the untreated control animals and compared with animals treated with one of the above-mentioned compounds or a salt thereof before, simultaneously with or after infection.

It is found that a prophylactic effect is achieved even when the compounds of the formula I are administered several days up to some weeks, for example four weeks, before infection, and that a therapeutic effect is still achieved when the compounds are administered several days, for example one week, after infection.

Also noteworthy is the broad viral spectrum against which the above-mentioned compounds are effective.

The compounds of the formula I can be used especially for the prophylaxis and treatment of diseases caused by the viruses specified below [for nomenclature see J. L. Melnick, Prog. med. Virol. 26, 214–232 (1980) and 28, 208–221 (1982)]:

DNA viruses with cubic symmetry and naked nucleocapsid, DNA viruses with encapsulated virion and RNA viruses with cubic symmetry and those with helical symmetry of the capsid.

The compounds of the formula I are preferably used in the case of DNA viruses with encapsulated virion and cubic symmetry of the capsid, in the case of RNA viruses with cubic symmetry of the capsid and naked virion and in the case of RNA viruses with helical symmetry of the capsid, in which the nucleocapsid capsule is positioned at the surface membrane, but also in the case of adenoviridae, poxviridae and coronaviridae, such as, especially, human corona viruses.

The compounds of the formula I are used especially in the case of herpesviridae, picornaviridae and myxo viruses, but also in the case of mastadeno viruses, such as, especially, human adeno viruses, in the case of chordopoxvirinae, such as, chiefly, orthopox viruses, such as, especially, for example, vaccinia viruses, in the case of reoviridae, above all (especially human) rota viruses, and in the case of caliciviridae and rhabdoviridae, such as, especially, vesiculo viruses in humans and also in horses, cattle and pigs.

The compounds of the formula I are used chiefly in the case of alpha-herpesvirinae, such as varicella viruses, for example human varicella-zoster viruses, rhino viruses, cardio viruses and ortho-myxoviridae, but also in the case of beta-herpesvirinae, such as, especially, human cytomegalo viruses, in the case of aphtho viruses, especially aphtho viruses in animals with cloven hooves, such as, especially, cattle, and in the case of para-myxoviridae, such as, especially, pneumo viruses, for example respiratory syncytial viruses in humans, and such as, also, morbilli viruses or para-myxo viruses, such as para-influenza viruses, for example human para-influenza viruses, including Sendai viruses, and in the case of arbo viruses or vesiculo viruses, for example *Vesicular stomatitis* viruses.

The compounds of the formula I are used very especially in the case of simplex viruses, for example human Herpes simplex viruses of types 1 and 2, in the case of human encephalomyocarditis viruses, in the case of influenza viruses, such as, especially, influenza A and influenza B viruses, and very especially in the case of the viruses mentioned in the Examples.

The compounds of the formula I can be used according to the invention by administering them enterally or parenterally, especially together with suitable adjuncts or carriers. They are preferably applied to the mucous membranes, for example intranasally, rectally or vaginally, or to the conjunctiva of the eye, or orally. However, the anti-viral effect also occurs in the case of administration by other routes, for example subcutaneously, intravenously or intramuscularly, or in the case of application to normal skin.

The dosage of the active ingredient depends, inter alia, on the species of warm-blooded animal, the organism's resistance, the method of administration and the type of virus. There is relatively little relationship between the dosage and the effect.

For prevention, a single dose of from approximately 0.01 mg to approximately 25 mg, preferably from 0.05 to 7 mg, for example 0.5 mg, of active ingredient is administered to a warm-blooded animal of approximately 70 kg body weight, for example a human. The prophylactic effect of this dose lasts for several weeks. If necessary, for example when there is an increased risk of infection, the administration of this dose can be repeated.

The therapeutic dose for warm-blooded animals of approximately 70 kg body weight is from 0.1 mg to 50 mg, preferably from 1 to 10 mg, for example 5 mg, especially in the case of oral administration. The dose in the case of topical, especially intranasal, administration is up to ten times lower. If necessary, the administration of these compounds of the formula I can be repeated until there is an improvement in the illness. Often, however, a single administration is sufficient.

The invention relates especially to the use of compounds of the formula I in which $R^1$ and $R^2$ each represents, independently of the other, hydrogen or $C_{1-2}$-alkyl, $R^3$ represents hydrogen, carboxy or benzyloxycarbonyl, $R^4$ represents hydrogen, benzyl, 2-aminoethyl, 2,3-dihydroxypropyl, trimethylsilyl, 2,3,4,5,6-pentahydroxycyclohexyl or 2-hydroxy-3-glycyloxypropyl, W represents hydrogen and Z represents a 1,2-dihydroxyethyl or 2-hydroxyethyl group in each of which the 2-hydroxy group is esterified by a straight-chain alkanoic acid having 6, 10, 12, 14, 16, 18 or 20 carbon atoms or by a straight-chain $C_{18}$-alkenoic acid having from 1 to 3 double bonds or is etherified by a straight-chain alkanol having 6, 8, 16 or 18 carbon atoms and in which the 1-hydroxy group, if present, is free or esterified by a staight-chain alkanoic acid having 6, 10, 12, 14, 16, 18 or 20 carbon atoms or by a straight-chain $C_{18}$-alkenoic acid having 1 or 2 double bonds or is etherified by a straight-chain alkanol having 1, 6, 8, 16 or 18 carbon atoms, or W represents hydroxymethyl or palmitoyloxymethyl and Z represents palmitoyloxymethyl, and to the use of pharmaceutically acceptable salts of these compounds, for the prophylaxis and treatment of virus infections in warm-blooded animals, such as, especially, in human beings.

The invention relates more especially to the use of the compounds of the formula I in which $R^3$ represents hydrogen, lower alkoxycarbonyl or carboxy and $R^4$ represents hydrogen, and to the use of their pharmaceutically acceptable salts, for the prophylaxis and treatment of virus infections.

The invention relates very especially to the use of compounds of the formula I in which $R^1$ and $R^2$ represent hydrogen, $R^3$ represents hydrogen or carboxy, $R^4$ represents hydrogen, W represents hydrogen and Z represents a 1,2-dihydroxyethyl group in which the 2-hydroxy group is esterified by a straight-chain $C_{14-18}$-alkanoic acid having an even number of carbon atoms or by a straight-chain singly unsaturated $C_{18}$-alkenoic acid or is etherified by a straight-chain alkanol having 16 or 18 carbon atoms, and in which the 1-hydroxy group is free or esterified by a straight-chain $C_{14-18}$-alkanoic acid having an even number of carbon atoms or by a straight-chain singly unsaturated $C_{18}$-alkenoic acid or is etherified by a straight-chain alkanol having 1, 16 or 18 carbon atoms, and to the use of their pharmaceutically acceptable salts.

Preferred is the use of compounds of the formula I in which W represents hydrogen and Z represents a 1,2-dihydroxyethyl group in which the 2-hydroxy group is esterified by a straight-chain $C_{14-18}$-alkanoic acid having an even number of carbon atoms or by a straight-chain singly unsaturated $C_{18}$-alkenoic acid and in which the 1-hydroxy group is either free or esterified by a straight-chain $C_{14-18}$-alkanoic acid having an even number of carbon atoms or by a straight-chain singly unsaturated $C_{18}$-alkenoic acid, and of their pharmaceutically acceptable salts.

Especially preferred is the use of compounds of the formula I in which W represents hydrogen and Z represents a 1,2-dihydroxyethyl group in which the two hydroxy groups are esterified by a straight-chain $C_{14-18}$-alkanoic acid having an even number of carbon atoms or by a straight-chain singly unsaturated $C_{18}$-alkenoic acid, or W and Z each represents a hydroxymethyl group that is esterified by a straight-chain $C_{14-18}$-alkanoic acid having an even number of carbon atoms or by a straight-chain singly unsaturated $C_{18}$-alkenoic acid, and of their pharmaceutically acceptable salts.

The invention relates very especially to the use of the compounds indicated in the following Tables 1 to 3 and in the Examples and to the use of their pharmaceutically acceptable salts.

The following abbreviations are used in Tables 1 to 3:

| Abbreviations | |
|---|---|
| Ara | n-eicosanoyl |
| Capri | caprinoyl (n-decanoyl) |
| Capro | capronyl (n-hexanoyl) |
| Capry | capryloyl (n-octanoyl) |
| Ela | trans-9-octadecenoyl |
| Laur | lauroyl |
| Lin | linoleoyl (9,12-octadecadienoyl) |
| Linolen | linolenoyl (9,12,15-octadecatrienoyl) |
| Myr | myristoyl |
| Ole | oleoyl |
| Palm | palmitoyl |
| Stea | stearoyl |

TABLE 1

$$\underset{R^2}{\overset{R^1}{\diagdown}}N-\underset{|}{\overset{R^3}{C}}H-CH_2-O-\underset{\underset{OR^4}{|}}{\overset{\overset{O}{\|}}{P}}-O-CH_2-\underset{|}{\overset{R^5}{C}}H-CH_2-O-R^6 \quad (II)$$

| $R^1$ | $R^2$ | $R^3$ | $R^4$ | $R^5$ | $R^6$ |
|---|---|---|---|---|---|
| H | H | H | H | O—Capri | Capri |
| H | H | H | H | O—Capry | Capry |
| H | H | H | H | O—Capro | Capro |
| H | H | H | H | O—Laur | Laur |
| H | H | H | H | O—Myr | Myr |
| H | H | H | H | O—Palm | Palm |
| H | H | H | H | O—Stea | Stea |
| H | H | H | H | O—Ara | Ara |
| H | H | H | H | O—Stea | n-$C_{16}H_{33}$ |
| H | H | H | H | O—Myr | n-$C_{16}H_{33}$ |
| H | H | H | H | O—Laur | n-$C_{16}H_{33}$ |
| H | H | H | H | O—Stea | n-$C_{18}H_{37}$ |
| H | H | H | H | O—Myr | n-$C_{18}H_{37}$ |
| H | H | H | H | O—Laur | n-$C_{18}H_{37}$ |
| $CH_3$ | H | H | H | O—Laur | Laur |
| $CH_3$ | H | H | H | O—Myr | Myr |
| $CH_3$ | H | H | H | O—Palm | Palm |
| $CH_3$ | H | H | H | O—Stea | Stea |
| $CH_3$ | H | H | H | O—Ara | Ara |
| $CH_3$ | H | H | H | O—n-$C_{16}H_{33}$ | n-$C_{16}H_{33}$ |
| $CH_3$ | $CH_3$ | H | H | O—Laur | Laur |
| $CH_3$ | $CH_3$ | H | H | O—Myr | Myr |
| $CH_3$ | $CH_3$ | H | H | O—Palm | Palm |
| $CH_3$ | $CH_3$ | H | H | O—Stea | Stea |
| $CH_3$ | $CH_3$ | H | H | O—Ara | Ara |
| $CH_3$ | $CH_3$ | H | H | O—n-$C_{16}H_{33}$ | n-$C_{16}H_{33}$ |
| $CH_3$ | $CH_3$ | H | H | O—Palm | Ole |
| H | H | H | H | OH | Palm |
| $CH_3$ | $CH_3$ | H | H | OH | Palm |
| H | H | H | H | H | Laur |
| H | H | H | H | H | Myr |
| H | H | H | H | H | Palm |
| H | H | H | H | H | Stea |
| H | H | H | H | H | Ara |
| $CH_3$ | H | H | H | H | Laur |
| $CH_3$ | H | H | H | H | Myr |
| $CH_3$ | H | H | H | H | Palm |
| $CH_3$ | H | H | H | H | Stea |
| $CH_3$ | H | H | H | H | Ara |
| $CH_3$ | $CH_3$ | H | H | H | Laur |
| $CH_3$ | $CH_3$ | H | H | H | Myr |
| $CH_3$ | $CH_3$ | H | H | H | Palm |
| $CH_3$ | $CH_3$ | H | H | H | Stea |
| $CH_3$ | $CH_3$ | H | H | H | Ara |
| H | H | H | H | O—n-$C_{16}H_{33}$ | n-$C_{16}H_{33}$ |
| H | H | H | H | $OCH_3$ | n-$C_{16}H_{33}$ |
| $CH_3$ | $CH_3$ | H | H | O—n-$C_8H_{17}$ | n-$C_8H_{17}$ |
| $CH_3$ | $CH_3$ | H | H | O—n-$C_6H_{13}$ | n-$C_6H_{13}$ |
| H | H | H | H | OH | Laur |
| H | H | H | H | OH | Myr |
| $CH_3$ | $C_2H_5$ | H | H | H | Laur |
| $C_2H_5$ | $C_2H_5$ | H | H | H | Laur |
| $CH_3$ | $C_2H_5$ | H | H | H | Myr |
| $C_2H_5$ | $C_2H_5$ | H | H | H | Myr |
| $CH_3$ | $C_2H_5$ | H | H | H | Palm |

TABLE 1-continued

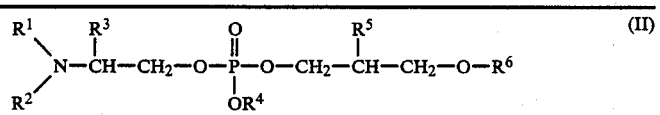

| R¹ | R² | R³ | R⁴ | R⁵ | R⁶ |
|---|---|---|---|---|---|
| C₂H₅ | C₂H₅ | H | H | H | Palm |
| H | H | H | H | O—Ela | Ela |
| H | H | H | H | O—Ole | Palm |
| CH₃ | CH₃ | H | H | O—Ole | Palm |
| CH₃ | C₂H₅ | H | H | O—Myr | Myr |
| CH₃ | C₂H₅ | H | H | O—Palm | Palm |
| CH₃ | C₂H₅ | H | H | O—Stea | Stea |
| C₂H₅ | C₂H₅ | H | H | O—Myr | Myr |
| C₂H₅ | C₂H₅ | H | H | O—Palm | Palm |
| C₂H₅ | C₂H₅ | H | H | O—Stea | Stea |
| H | H | H | H | O—Palm | n-C₁₆H₃₃ |
| H | H | H | H | O—Palm | n-C₁₈H₃₇ |
| H | H | COOH | —CH₂CH₂—CH₂ | O—Palm | Palm |
| H | H | H | —CH₂—CH(OH)—CH₂OH | O—Palm | Palm |
| H | H | H | Si(CH₃)₃ | O—Palm | Palm |
| H | H | H | 2,3,4,5,6-pentahydroxycyclohexyl | O—Stea | Stea |
| H | H | H | benzyl | O—Palm | Palm |
| H | H | H | CH₂—CH(OH)—CH₂O—C(=O)—CH₂—NH₂ | O—Stea | Stea |
| H | H | COOH | H | O—Ole | Ole |
| H | H | COOH | H | O—Lin | Lin |
| H | H | COOH | H | O—Myr | Myr |
| H | H | COOH | H | O—Capro | Capro |
| H | H | COOH | H | O—Capri | Capri |
| H | H | COOH | H | O—Laur | Laur |
| H | H | COOH | H | O—Palm | Palm |
| H | H | COOH | H | O—Stea | Stea |
| H | H | COOH | H | O—Palm | Ole |
| H | H | COOH | H | O—Palm | Lin |
| H | H | COOH | H | O—Palm | Linolen |

TABLE 2

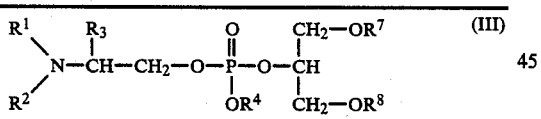

| R¹ | R² | R₃ | R⁴ | R⁷ | R⁸ |
|---|---|---|---|---|---|
| H | H | H | H | Palm | Palm |
| CH₃ | H | H | H | Palm | Palm |
| CH₃ | CH₃ | H | H | Palm | Palm |
| H | H | H | H | Palm | H |
| H | H | H | H | H | Palm |

TABLE 3

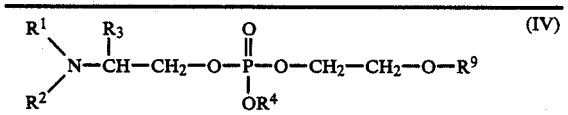

| R¹ | R² | R₃ | R⁴ | R⁹ |
|---|---|---|---|---|
| H | H | H | H | Laur |
| H | H | H | H | Myr |
| H | H | H | H | Palm |
| CH₃ | H | H | H | Palm |
| CH₃ | CH₃ | H | H | Palm |
| H | H | H | H | Stea |

The invention also relates to cephalin derivatives of the formula I

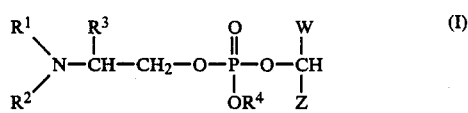

in which $R^1$ and $R^2$ each represents, independently of the other, hydrogen or lower alkyl, $R^3$ represents hydrogen, lower alkoxycarbonyl, carbamoyl or free or protected carboxy, $R^4$ represents hydrogen or an aliphatic, aromatic, aromatic-aliphatic or cycloaliphatic radical, W represents hydrogen and Z represents a 1,2-dihydroxyethyl, 2-hydroxyethyl or hydroxymethyl group in which at least one hydroxy group is esterified by an aliphatic $C_{6-30}$-carboxylic acid or etherified by an aliphatic $C_{6-30}$-alcohol and in which the other hydroxy group, if present, is free, esterified by an aliphatic $C_{2-30}$-carboxylic acid or etherified by an aliphatic $C_{1-30}$-alcohol, or W represents hydroxymethyl or a hydroxymethyl group that is esterified by an aliphatic $C_{6-30}$-carboxylic acid or etherified by an aliphatic $C_{6-30}$-alcohol and Z represents a hydroxymethyl group that is esterified by an aliphatic $C_{6-30}$-carboxylic acid or etherified by an aliphatic $C_{6-30}$-alcohol, $R^1$ being other than hydrogen and $C_{1-2}$-alkyl, or $R^2$ being other than hydrogen and $C_{1-2}$-alkyl, or $R^3$ being other than hydrogen, carboxy and benzyloxycarbonyl, or $R^4$ being other than hydrogen, benzyl, 2-aminoethyl, 2,3-dihydroxypropyl, trimethylsilyl, 2,3,4,5,6-pentahydroxycyclohexyl and 2-hydroxy-3-glycyloxypropyl, or, if W represents hydrogen, Z being other than a 1,2-dihydroxyethyl and 2-hydroxyethyl group in each of which the 2-hydroxy group is esterified by a straight-chain alkanoic acid having 6, 10, 12, 14, 16, 18 or 20 carbon atoms or by a straight-chain $C_{18}$-alkenoic acid having from 1 to 3 double bonds or is etherified by a straight-chain alkanol having 6, 8, 16 or 18 carbon atoms and in which the 1-hydroxy group, if present, is free or esterified by a straight-chain alkanoic acid having 6, 10, 12, 14, 16, 18 or 20 carbon atoms or by a straight-chain $C_{18}$-alkenoic acid having 1 or 2 double bonds or is etherified by a straight-chain alkanol having 1, 6, 8, 16 or 18 carbon atoms, or, if W does not represent hydrogen, W being other than palmitoyloxymethyl and hydroxymethyl, or, if W does not represent hydrogen, Z being other than palmitoyloxymethyl, and to salts of these compounds.

The invention relates especially to compounds of the formula I in which $R^1$ and $R^2$ each represents, independently of the other, hydrogen or lower alkyl, $R^3$ represents hydrogen, carboxy or lower alkoxy-carbonyl, $R^4$ represents hydrogen, and W and Z each represents hydroxymethyl esterified by a straight-chain $C_{6-22}$-alkanoic acid that is other than palmitic acid or by a straight-chain $C_{18}$-alkenoic acid having from 1 to 3 double bonds, and to their pharmaceutically acceptable salts.

The invention relates more especially to the last-mentioned compounds of the formula I in which $R^2$ represents lower alkyl other than methyl and/or $R^3$ represents carboxy or lower alkoxycarbonyl, and the other substituents have the meanings mentioned in the previous section, and to their pharmaceutically acceptable salts.

The cephalin derivatives of the formula I and their salts are manufactured according to methods known per se. They are obtained, for example, as follows:

(a) for the manufacture of a compound of the formula I in which at least one of the radicals $R^1$ and $R^2$ represents lower alkyl, a compound of the formula V

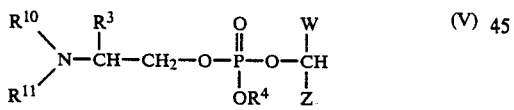

in which at least one of the radicals $R^{10}$ and $R^{11}$ represents hydrogen and the other of the radicals $R^{10}$ and $R^{11}$ represents hydrogen or lower alkyl and the other substituents have the meanings mentioned above (functional groups present in a compound of the formula V, with the exception of the group participating in the reaction, if necessary being in protected form) is alkylated, and, if necessary, protecting groups present are removed, or (b) a compound of the formula VI

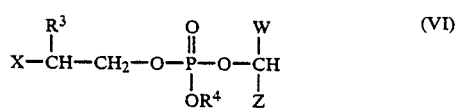

in which X represents a nucleophilic leaving group and the other substituents have the meanings mentioned above (functional groups present in a compound of the formula VI, with the exception of the group participating in the reaction, if necessary being in protected form) is reacted with a compound of the formula VII

in which the substituents have the meanings mentioned above, or with a reactive derivative thereof, and, if necessary, protecting groups present are removed, or (c) a compound of the formula VIII

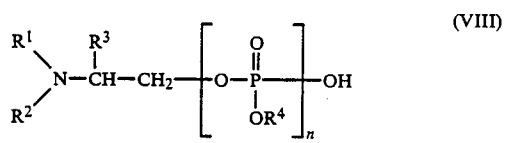

in which n has the meaning mentioned below and the other substituents have the meanings mentioned above (functional groups present in a compound of the formula VIII, with the exception of the group participating in the reaction, if necessary being in protected form) or a reactive derivative thereof, is reacted with a compound of the formula IX

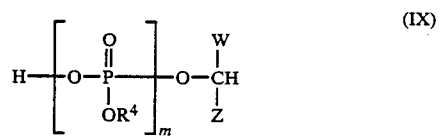

in which m represents 1 if, in the reactant of the formula VIII, n represents 0, or in which m represents 0 if n represents 1, and the other substituents have the meanings mentioned above (functional groups present in a compound of the formula IX, with the exception of the group participating in the reaction, if necessary being in protected form) or with a reactive derivative thereof, and, if necessary, protecting groups present are removed, or (d) a compound of the formula X

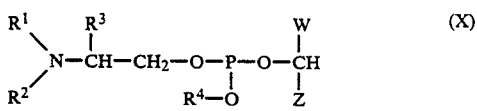

in which the substituents have the meanings mentioned above (functional groups present in a compound of the formula X, with the exception of the group participating in the reaction, if necessary being in protected form), or a tautomer of a compound of the formula X, is oxidised with an oxidising agent, and, if necessary, protecting groups present are removed, or (e) a compound of the formula XI

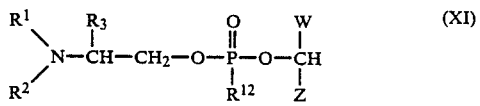

in which R[12] represents halogen and the other substituents have the meanings mentioned above (functional groups present in a compound of the formula XI, with the exception of the group participating in the reaction, if necessary being in protected form) is hydrolysed, and, if necessary, protecting groups present are removed, or (f) a compound of the formula XII

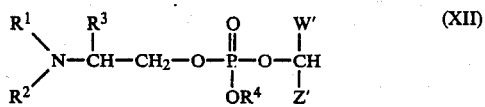

in which W' represents hydrogen and Z' represents 1,2-dihydroxyethyl, 2-hydroxyethyl, hydroxymethyl, or 1,2-dihydroxyethyl in which one of the two hydroxy groups is esterified or etherified as described above, or at least one of the radicals W' and Z' represents free hydroxymethyl and the other of the radicals W' and Z' represents free hydroxymethyl or hydroxymethyl that is esterified or etherified as described above, and the other substituents have the meanings mentioned above (functional groups present in a compound of the formula XII, with the exception of the group participating in the reaction, if necessary being in protected form) or a reactive derivative thereof, is esterified with an aliphatic carboxylic acid or with a reactive derivative thereof or is etherified with an aliphatic alcohol or with a reactive derivative thereof, and, if necessary, protecting groups present are removed, or (g) for the manufacture of a compound of the formula I in which W represents hydrogen and Z represents a 1,2-dihydroxyethyl group in which the 2-hydroxy group is esterified by an aliphatic $C_{6-30}$-carboxylic acid, and $R^1$, $R^2$, $R^3$ and $R^4$ have the meanings mentioned above, a compound of the formula I in which W represents hydrogen and Z represents a 1,2-dihydroxyethyl group in which the 2-hydroxy group is esterified by an aliphatic $C^{6-30}$-carboxylic acid and the 1-hydroxy group is esterified by an aliphatic $C^{2-30}$-carboxylic acid, and $R^1$, $R^2$, $R^3$ and $R^4$ have the meanings mentioned above, is reacted with an enzyme that removes the 1-acyl group regioselectively, or (h) in a compound of the formula I in which the substituents have the meanings mentioned above, it being necessary in a compound of the formula I for at least one functional group to be protected by a readily removable protecting group, the protecting group(s) is (are) removed, and, after carrying out one of the above-mentioned process variants (a-h), for the manufacture of a salt, if necessary a compound of the formula I is converted into a salt, or, in order to convert a compound of the formula I or a salt thereof into a different compound of the formula I or into a salt thereof, a carboxy group contained in the radical $R^3$ is esterified or amidated.

The process variants mentioned above are described in more detail in the following:

GENERAL INFORMATION

Functional groups, which are protected if necessary, are especially carboxy, hydroxy, amino and/or the phosphoric acid group.

Carboxy-protecting groups are, for example, those mentioned above.

Hydroxy-protecting groups are, for example, acyl radicals, such as optionally substituted, for example halo-substituted, lower alkanoyl, such as 2,2-dichloroacetyl, or acyl radicals of carbonic acid semi-esters, especially tert.-butoxycarbonyl, optionally substituted benzyloxycarbonyl or diphenylmethoxycarbonyl, for example 4-nitrobenzyloxycarbonyl, or 2-halo-lower alkoxycarbonyl, such as 2,2,2-trichloroethoxycarbonyl, also trityl or formyl, or organic silyl or stannyl radicals, also readily removable etherifying groups, such as tert.-lower alkyl, for example tert.-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding thia analogues, and also optionally substituted 1-phenyl-lower alkyl, such as optionally substituted benzyl or diphenylmethyl, there being suitable as substituents of the phenyl radicals, for example, halogen, such as chlorine, lower alkoxy, such as methoxy, and/or nitro.

The organic silyl or stannyl radicals mentioned hereinbefore and hereinafter preferably contain lower alkyl, especially methyl, as substituent of the silicon or tin atoms. Corresponding silyl or stannyl groups are especially tri-lower alkylsilyl, especially trimethylsilyl, also dimethyl-tert.-butylsilyl, or correspondingly substituted stannyl, for example tri-n-butylstannyl.

A protected amino group can be, for example, in the form of a readily cleavable acylamino, arylmethylamino, etherified mercaptoamino, 2-acyl-lower alk-1-enylamino, silylamino or stannylamino group or in the form of an azido group.

In a corresponding acylamino group, acyl is, for example, the acyl radical of an organic carboxylic acid having, for example, up to 18 carbon atoms, especially an alkanecarboxylic acid optionally substituted, for example, by halogen or aryl, or of benzoic acid optionally substituted, for example, by halogen, lower alkoxy or nitro, or of a carbonic acid semi-ester. Such acyl groups are, for example, lower alkanoyl, such as formyl, acetyl or propionyl, halo-lower alkanoyl, such as 2-haloacetyl, especially 2-chloro-, 2-bromo-, 2iodo-, 2,2,2-trifluoro- or 2,2,2-trichloro-acetyl, benzoyl optionally substituted, for example, by halogen, lower alkoxy or by nitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert.-lower alkoxycarbonyl, for example tert.-butoxycarbonyl, arylmethoxycarbonyl having one or two aryl radicals that are preferably phenyl optionally mono- or poly-substituted, for example, by lower alkyl, especially tert.-lower alkyl, such as tert.-butyl, lower alkoxy, such as methoxy, hydroxy, halogen, for example chlorine, and/or by nitro, such as optionally substituted benzyloxycarbonyl, for example 4- nitrobenzyloxycarbonyl, or substituted diphenyl-methoxycarbonyl, for example benzhydryloxycarbonyl or di-(4-methoxyphenyl)-methoxycarbonyl, aroylmethoxycarbonyl in which the aroyl group preferably represents benzoyl optionally substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)ethoxycarbonyl in which each of the substituents, independently of the others, represents an aliphatic, araliphatic, cycloaliphatic or aromatic hydrocarbon radical that has up to 15 carbon atoms and is optionally substituted, for example, by lower alkyl, lower alkoxy, aryl, halogen or by nitro, such as corresponding optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butylmethylsilyl)-ethoxycarbonyl, or 2-triarylsilylethoxycarbonyl, such as 2-triphenylsilylethoxycarbonyl.

Further acyl radicals coming into consideration as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, optionally substituted diphenylphosphoryl, for example diphenylphosphoryl, di-(phenyl-lower alkyl)-phosphoryl that is optionally substituted, for example, by nitro, for example dibenzylphosphoryl or di-(4-nitrobenzyl)-phosphoryl, optionally substituted phenoxyphenylphosphonyl, for example phenoxyphenylphosphonyl, di-lower alkylphosphinyl, for example diethylphosphinyl, or optionally substituted diphenylphosphinyl, for example diphenylphosphinyl.

In an arylmethylamino group that is a mono-, di-or especially tri-arylmethylamino group, the aryl radicals are especially optionally substituted phenyl radicals. Such groups are, for example, benzylamino, diphenylmethylamino and especially tritylamino.

An etherified mercapto group in an amino group protected by such a radical is especially arylthio or aryl-lower alkylthio in which aryl is especially phenyl that is optionally substituted, for example, by lower alkyl, such as methyl or tert.-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that may be used as an amino-protecting group, acyl is, for example, the corresponding radical of a lower alkanecarboxylic acid, of benzoic acid that is optionally substituted, for example, by lower alkyl, such as methyl or tert.-butyl, lower alkoxy, such as methoxy, halogen, such as chlorine, and/or by nitro, or especially of a carbonic acid semi-ester, such as a carbonic acid lower alkyl semiester. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonylprop-1-en-2-yl.

An amino goup can also be protected in protonated form; as corresponding anions there come into consideration especially those of strong inorganic acids, such as hydrohalic acids, for example the chlorine or bromine anion, or organic sulphonic acids, such as p-toluenesulphonic acid.

Preferred amino-protecting groups are acyl radicals of carbonic acid semi-esters, especially tert.-butoxycarbonyl, or benzyloxycarbonyl or diphenylmethoxycarbonyl each of which is optionally substituted, for example as indicated, for example 4-nitrobenzyloxycarbonyl, or 2-halo-lower alkoxycarbonyl, such as 2,2,2trichloroethoxycarbonyl, also trityl or formyl.

The phosphoric acid group is preferably protected in esterified form, the esterifying radicals being preferably of aliphatic, aromatic or aromatic-aliphatic nature, for example lower alkyl, such as, especially, methyl, phenyl that is optionally substituted, for example, by nitro or halogen, or benzyl that is optionally substituted, for example, by nitro or halogen.

The removal of the above-mentioned protecting groups is carried out, for example, as described below in Process g. Process a:

The alkylation of the amino group in a compound of the formula V is carried out, for example, using one of the agents mentioned below.

Suitable agents are, for example, corresponding diazo compounds, such as optionally substituted diazo-lower alkanes, for example diazomethane, diazoethane, diazo-n-butane or diphenyldiazomethane. These reagents are used in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofuran or dioxan, or in the presence of a solvent mixture, and depending on the diazo reagent used, while cooling, at room temperature or while heating slightly, also, if necessary, in a closed vessel and/or under an inert gas atmosphere, for example a nitrogen atmosphere.

Further suitable agents are esters of corresponding alcohols, especially those with strong inorganic or organic acids, such as mineral acids, for example hydrohalic acids, such as hydrochloric acid, hydrobromic acid or hydriodic acid, also sulphuric acid, or halosulphuric acid, for example fluorosulphuric acid, or strong organic sulphonic acids, such as lower alkanesulphonic acids that are optionally substituted, for example, by halogen, such as fluorine, or aromatic sulphonic acids, such as, for example, benzenesulphonic acids optionally substituted by lower alkyl, such as methyl, halogen, such as bromine, and/or by nitro, for example methanesulphonic, trifluoromethanesulphonic or p-toluenesulphonic acid. Such esters are, inter alia, lower alkyl halides, di-lower alkyl sulphates, such as dimethyl sulphate, also fluorosulphonic acid esters, such as fluorosulphonic acid lower alkyl esters, for example fluorosulphonic acid methyl ester, or optionally halo-substituted methanesulphonic acid lower alkyl esters, for example trifluoromethanesulphonic acid methyl ester. They are customarily used in the presence of an inert solvent, such as an optionally halogenated, such as chlorinated, aliphatic, cycloaliphatic or aromatic hydrocarbon, for example methylene chloride, an ether, such as dioxan or tetrahydrofuran, or a mixture thereof. There are preferably also used suitable condensation agents, such as alkali metal carbonates or bicarbonates, for example sodium or potassium carbonate or bicarbonate (usually together with a sulphate), or organic bases, such as tri-lower alkylamines which are customarily sterically hindered, for example N,N-diisopropyl-N-ethylamine (preferably together with halosulphonic acid lower alkyl esters or optionally halo-substituted methanesulphonic acid lower alkyl esters), the operation being carried out while cooling, at room temperature or while heating, for example at temperatures of from approximately −20° C. to approximately 50° C., and, if necessary, in a closed vessel and/or in an inert gas atmosphere, for example a nitrogen atmosphere.

Further agents are corresponding tri-substituted oxonium salts (so-called Meerwein salts) or di-substituted carbenium or halonium salts in which the substituents are the etherifying radicals, for example tri-lower alkyloxonium salts and di-lower alkoxycarbenium or di-lower alkylhalonium salts, especially the corresponding salts with complex fluorine-containing acids, such as the corresponding tetrafluoroborates, hexafluorophosphates, hexafluoroantimonates or hexachloroantimonates. Such reagents are, for example, trimethyloxonium or triethyloxonium hexafluoroantimonate, hexachloroantimonate, hexafluorophosphate or tetrafluoroborate, dimethoxycarbenium hexafluorophosphate or dimethylbromonium hexafluoroantimonate. These agents are preferably used in an inert solvent, such as an ether or a halogenated hydrocarbon, for example diethyl ether, tetrahydrofuran or methylene chloride, or in a mixture thereof, if necessary in the presence of a base, such as an organic base, for example a tri-lower alkylamine which is preferably sterically hindered, for example N,N-diisopropyl-N-ethylamine, and while cooling, at room temperature or while heating slightly, for example at from approximately $-20°$ C. to approximately $50°$ C., if necessary in a closed vessel and/or in an inert gas atmosphere, for example a nitrogen atmosphere.

Process b:

A nucleophilic leaving group X is especially hydroxy esterified by suitable acids.

Reactive esterified hydroxy is, for example, hydroxy esterified by a strong inorganic or organic acid, such as hydroxy esterified by a mineral acid, for example a hydrohalic acid, such as hydrochloric acid, hydrobromic acid or hydriodic acid, also sulphuric acid, or halosulphuric acid, for example fluorosulphuric acid, or by a strong organic sulphonic acid, such as a lower alkanesulphonic acid that is optionally substituted, for example, by halogen, such as fluorine, or an aromatic sulphonic acid, for example a benzenesulphonic acid that is optionally substituted by lower alkyl, such as methyl, halogen, such as bromine, and/or by nitro, for example a methanesulphonic, trifluoromethanesulphonic or p-toluenesulphonic acid, and is preferably a chloride, bromide or iodide.

Process c:

A reactive derivative of a compound of the formula VIII in which n represents 1 or of a compound of the formula IX in which m represents 1 is, for example, a mono- or bis-anhydride with a strong acid, especially a mineral acid, such as, particularly, a hydrohalic acid, such as, chiefly, hydrochloric acid. The second acidic phosphoric acid group may be present as such or it may be in the form of an anhydride as described above or in esterified form, there being preferred as esterifying radicals those that can be removed regioselectively when the reaction between compounds VIII and IX is complete, for example the methyl ester group which can be removed, for example, by means of lithium bromide, or radicals that can be removed electrochemically, for example benzyl ester or phenyl ester radicals.

The formation of reactive phosphoric acid derivatives can also be carried out in situ in the presence of compounds that, with phosphoric acid or monoesters thereof, are capable of being converted into reactive compounds of anhydride or enol ester-like character at least intermediately, for example in the presence of p-toluenesulphonic acid chloride, cyanuric chloride, N-alkyl-5-phenylisoxazolium salts, ethoxyacetylene or preferably trichloroacetonitrile or especially a carbodiimide, such as, especially, dicyclohexyl carbodiimide. For example, it is possible to react a phosphoric acid monoester of the formula VIII or IX in which n and m represent 1 with excess alcohol of the formula IX or VIII, respectively, in which n and m represent 0, in the presence of several times the molar amount, for example five times the molar amount, of dicyclohexyl carbodiimide in the presence or absence of a tertiary amine.

If both acidic groups in a phosphoric acid monoester are in the form of an anhydride with a hydrohalic acid, it is possible first of all to obtain, in addition to the triester, also phosphoric acid diester halides which can then be hydrolysed to form diesters using water or water-yielding agents or by heating with tertiary alcohols, such as tert.-butanol or tetrahydropyranol.

If a phosphoric acid monoester dihalide, for example a phosphoric acid monoester dichloride, is used as starting material, the reaction is preferably carried out in the presence of a tertiary amine, such as triethylamine, pyridine, lutidine or quinoline, an additional activation of the ester chloride being brought about by dimethylformamide.

A preferred embodiment of Process c is the reaction of a phosphoric acid monoester dichloride with the corresponding alcohol in the presence of a tertiary amine followed by hydrolysis of the phosphoric acid diester halide which is formed first.

In a reactive derivative of a compound of the formula VIII or IX in which n and m represent 0, the hydroxy group participating in the reaction is in reactive esterified form.

Reactive esterified hydroxy is, for example, hydroxy esterified as described in Process b.

The reaction can be carried out as follows: a reactive phosphoric acid derivative of the formula VIII or IX is reacted with an alcohol of the formula IX or VIII, respectively, in unactivated form, or a reactive esterified alcohol of the formula VIII or IX is reacted with a phosphoric acid derivative of the formula IX or VIII, respectively, in unactivated form, or with a reactive salt thereof.

In view of the intended nucleophilic substitution reaction, there are used as salts of compounds of the formula VIII or IX salts that are particularly reactive, for example salts, such as silver salts, that are capable of forming a sparingly soluble precipitate with the nucleophilic leaving group in the co-reactant, for example one of the above-mentioned halide ions, or salts with a large cation, for example caesium salts in which the nucleophilic character of the phosphate radical is increased. In order to increase the nucleophilic character of the phosphate radical, it is also possible to distance the ion of opposite charge, for example by the addition of complex-formers, such as Crown ethers, for example 18-Crown-6. When using 18- c Crown-6 it is possible to carry out the reaction with a potassium salt.

A preferred embodiment of Process b is the reaction of the caesium or silver salt of a phosphoric acid monoester of the formula VIII or IX in which one of the two acidic groups is protected by a readily removable protecting group, for example one of those described above, for example in the form of a benzyl or phenyl ester, with a reactive alcohol of the formula IX or VIII, respectively, in which the OH group has been replaced by chlorine, bromine or iodine. After the completion of the reaction, the protecting group, for example a benzyl or phenyl ester protecting group as described above, is removed.

Process d:

The compounds of the formula X in which $R^4$ represents hydrogen are for the most part in the tautomeric form in which a proton is bonded directly to phosphorus. The oxidation can be carried out, for example, using aqueous potassium permanganate at temperatures of approximately 0° C. In aqueous medium, inter alia alkali iodates, alkali periodates and alkali hypochlorites, peracetic acid and N-chloro-4-methylbenzenesulphonic acid amide are also suitable as oxidising agents.

Process e:

In a compound of the formula XI, $R^{12}$ represents a halogen, such as bromine or iodine, bu especially chlorine.

The hydrolysis is carried out with water or a water-yielding agent, preferably at elevated temperature, for example at from 30 to 95° C.

The starting materials can be obtained, for example, as described in Process c or by chlorination of the corresponding phosphorous acid diesters, for example using elemental chlorine.

Process f:

In a reactive derivative of a compound of the formula XII, the hydroxy group participating in the reaction is in reactive esterified form, for example as described in Process b.

Reactive carboxylic acid derivatives are especially reactive activated esters or reactive anhydrides, also reactive cyclic amides; it is also possible to form reactive carboxylic acid derivatives in situ.

Activated esters of acids are especially esters that are unsaturated at the linking carbon atom of the esterifying radical, for example of the vinyl ester type, such as actual vinyl esters (which can be obtained, for example, by transesterification of a corresponding ester with vinyl acetate; activated vinyl ester method), carbamoylvinyl esters (which can be obtained, for example, by treating the corresponding acid with an isoxazolium reagent; 1,2-oxazolium or Woodward method), or 1-lower alkoxyvinyl esters (which can be obtained, for example, by treating the corresponding acid with a lower alkoxyacetylene; ethoxyacetylene method), or esters of the amidino type, such as N,N'-disubstituted amidino esters (which can be obtained, for example, by treating the corresponding acid with a suitable N,N'-disubstituted carbodiimide, for example N,N'-dicyclohexyl carbodiimide; carbodiimide method), or N,N-disubstituted amidino esters (which can be obtained, for example, by treating the corresponding acid with an N,N-disubstituted cyanamide; cyanamide method), suitable aryl esters, especially phenyl esters suitably substituted by electron-attracting substituents (which can be obtained, for example, by treating the corresponding acid with a suitably substituted phenol, for example 4-nitrophenol, 4-methylsulphonylphenol, 2,4,5-trichlorophenol, 2,3,4,5,6-pentachlorophenol or 4-phenyldiazophenol, in the presence of a condensation agent, such as N,N'-dicyclohexyl carbodiimide; activated aryl esters method), cyanomethyl esters (which can be obtained, for example, by treating the corresponding acid with chloroacetonitrile in the presence of a base; cyanomethyl esters method), thioesters, especially phenylthioesters optionally substituted, for example, by nitro (which can be obtained, for example, by treating the corresponding acid with thiophenols that are optionally substituted, for example, by nitro, inter alia with the aid of the anhydride or carbodiimide method; activated thioesters method), or amino or amido esters (which can be obtained, for example, by treating the corresponding acid with an N-hydroxyamino or N-hydroxyamido compound, for example N-hydroxysuccinimide, N-hydroxypiperidine, N-hydroxyphthalimide or 1-hydroxybenzotriazole, for example according to the anhydride or carbodiimide method; activated N-hydroxyesters method), or silyl esters (which can be obtained, for example, by treating the corresponding acid with a silylating agent, for example hexamethyldisilazane).

Anhydrides of acids may be symmetrical or, preferably, mixed anhydrides of these acids, for example anhydrides with inorganic acids, such as acid halides, especially acid chlorides (which can be obtained, for example, by treating the corresponding acid with thionyl chloride, phosphorus pentachloride or oxalyl chloride; acid chloride method), azides (which can be obtained, for example, from a corresponding acid ester by way of the corresponding hydrazide and the treatment of the latter with nitrous acid; azide method), anhydrides with carbonic acid semi-derivatives, such as with corresponding esters, for example carbonic acid lower alkyl semi-esters (which can be obtained, for example, by treating the corresponding acid with haloformic acid lower alkyl esters, such as chloroformic acid lower alkyl esters, or with a 1-lower alkoxycarbonyl-2-lower alkoxy-1,2-dihydroquinoline, for example 1-lower alkoxycarbonyl-2-ethoxy-1,2-dihydroquinoline; mixed 0-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anhydrides with organic carboxylic acids (which can be obtained, for example, by treating the corresponding acid with an optionally substituted lower alkanecarboxylic acid halide or phenylalkanecarboxylic acid halide, for example phenylacetic acid chloride, pivalic acid chloride or trifluoroacetic acid chloride; mixed carboxylic acid anhydrides method) or with organic sulphonic acids (which can be obtained, for example, by treating a salt, such as an alkali metal salt, of the corresponding acid with a suitable organic sulphonic acid halide, such as lower alkanesulphonic acid chloride or arylsulphonic acid chloride, for example methane- or p-toluene-sulphonic acid chloride; mixed sulphonic acid anhydrides method), and symmetrical anhydrides (which can be obtained, for example, by condensing the corresponding acid in the presence of a carbodiimide or of 1-diethylaminopropine; symmetrical anhydrides method).

Suitable cyclic amides are especially amides having five-membered diazacycles of aromatic character, such as amides with imidazoles, for example imidazole (which can be obtained, for example, by treating the corresponding acid with N,N'-carbonyldiimidazole; imidazolide method), or pyrazoles, for example 3,5-dimethylpyrazole (which can be obtained, for example, by way of the acid hydrazide by treatment with acetylacetone; pyrazolide method).

As mentioned, reactive carboxylic acid derivatives can also be formed in situ. For example, N,N'-disubstituted amidino esters can be formed in situ by reacting a mixture of the starting material of the formula XII and the aliphatic carboxylic acid in the presence of a suitable N,N-disubstituted carbodiimide, for example N,N'-dicyclohexyl carbodiimide. It is also possible to form amino or amido esters of the aliphatic carboxylic acid in the presence of the starting material of the formula XII to be acylated by reacting a mixture of the starting materials in the presence of an N,N'-disubstituted carbodiimide, for example N,N'-dicyclohexyl carbodiimide, and an N-hydroxyamine or N-hydroxyamide, for example N-hydroxysuccinimide, optionally in the presence of a suitable base, for example 4-dimethylaminopyridine.

A reactive derivative of the aliphatic alcohol is, for example, an alcohol in which the hydroxy group is in reactive esterified form, for example as described in Process b. Suitable agents for etherifying a hydroxy group in the radical W' or Z' are, for example, also the agents mentioned in Process a. The reaction is carried out, for example, as follows: a compound of the formula XII is reacted in unactivated form with the reactive carboxylic acid or alcohol derivative, it also being possible for the activation of the carboxylic acid to be carried out in situ, in the presence of the compound of the formula XII, for example as described above. The reaction can alternatively be carried out as follows: a compound of the formula XII in which the hydroxy group(s) participating in the reaction is(are) in reactive esterified form, for example in the form of a halide, is reacted with a carboxylic acid or an alcohol, in each case in unactivated form, or with a reactive carboxylic acid salt, for example a caesium salt.

Process g:

The reaction is carried out, for example, with the enzyme phospholipase $A_2$ in the presence of calcium chloride.

Process h:

Functional groups in a compound of the formula I which are optionally protected by a readily removable protecting group are especially an amino group $N(R^1, R^2)$, free carboxy $R^3$, the phosphoric acid group or free hydroxy in the radical W or Z. Protecting groups for the functional groups mentioned are, for example, those mentioned above under "General Information".

The removal of the protecting groups is carried out in a manner known per se, for example by means of solvolysis, especially hydrolysis, alcoholysis or acidolysis, or by means of reduction, especially hydrogenolysis or chemical or electrochemical reduction, or enzymatically, in stages or simultaneously.

Thus, tert.-lower alkoxycarbonyl, or lower alkoxycarbonyl substituted in the 2-position by an organic silyl group or in the 1-position by lower alkoxy or lower alkylthio, or optionally substituted diphenylmethoxycarbonyl can be converted into free carboxy, for example, by treatment with a suitable acid, such as formic acid or trifluoroacetic acid, optionally with the addition of a nucleophilic compound, such as phenol or anisole. Optionally substituted benzyloxycarbonyl can be freed, for example, by hydrogenolysis, that is to say by treatment with hydrogen in the presence of a metallic hydrogenation catalyst, such as a palladium catalyst. In addition, suitably substituted benzyloxycarbonyl, such as 4-nitrobenzyloxycarbonyl, can be converted into free carboxy by chemical reduction, for example by treatment with an alkali metal dithionite, for example sodium dithionite, or with a reducing metal, for example zinc, or a reducing metal salt, such as a chromium(II) salt, for example chromium(II) chloride, usually in the presence of an agent that yields hydrogen and that, together with the metal, is capable of producing nascent hydrogen, such as an acid, especially a suitable carboxylic acid, such as a lower alkanecarboxylic acid optionally substituted, for example, by hydroxy, for example acetic acid, formic acid, glycolic acid, diphenylglycolic acid, lactic acid, mandelic acid, 4-chloromandelic acid or tartaric acid, or an alcohol or thiol, water preferably being added. By treatment with a reducing metal or metal salt, as described above, it is also possible to convert 2-halo-lower alkoxycarbonyl (optionally after conversion of a 2-bromo-lower alkoxycarbonyl group into a corresponding 2-iodo-lower alkoxycarbonyl group) or aroylmethoxycarbonyl into free carboxy, it being possible to cleave aroylmethoxycarbonyl also by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid yielding the fluoride anion, such as an alkali metal fluoride, for example sodium or potassium fluoride, in the presence of a macrocyclic polyether ("Crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic polar solvent, such as dimethyl sulphoxide or N,N-dimethylacetamide. Carboxy esterified by an organic silyl group, such as tri-lower alkylsilyl, for example trimethylsilyl, can be freed in customary manner by solvolysis, for example by treatment with water, an alcohol or an acid.

A protected amino group is freed in a manner known per se and, depending on the nature of the protecting groups, by various methods, but preferably by solvolysis or reduction. 2-halo-lower alkoxycarbonylamino (optionally after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with an alkali metal dithionite, for example sodium dithionite. Optionally substituted diphenylmethoxycarbonylamino, tert.-lower alkoxycarbonylamino or 2-trisubstituted silylethoxycarbonylamino can be freed by treatment with a suitable acid, for example formic acid or trifluoroacetic acid, optionally substituted benzyloxycarbonylamino can be freed, for example, by hydrogenolysis, that is to say by treatment with hydrogen in the presence of a suitable hydrogenation catalyst, such as a palladium catalyst, optionally substituted triarylmethylamino or formylamino can be freed, for example, by treatment with an acid, such as a mineral acid, for example hydrochloric acid, or an organic acid, for example formic, acetic or trifluoroacetic acid, optionally in the presence of water, and an amino group protected by an organic silyl group can be freed, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea, and by subsequent solvolysis, such as alcoholysis or hydrolysis, of the resulting condensation product. An amino group protected by 2-substituted silylethoxycarbonyl can also be converted into the free amino group by treatment with a salt of hydrofluoric acid yielding fluoride anions, as indicated above in connection with the freeing of a correspondingly protected carboxy group.

Amino protected in the form of an azido group is converted into free amino, for example by reduction, for example by catalytic hydrogenation with hydrogen in the presence of a hydrogenation catalyst, such as platinum oxide, palladium or Raney nickel, or alternatively by treatment with zinc in the presence of an acid, such as acetic acid. The catalytic hydrogenation is preferably carried out in an inert solvent, such as a halogenated hydrocarbon, for example methylene chloride, or alternatively in water or a mixture of water and an organic solvent, such as an alcohol or dioxan, at approximately from 20° C. to 25° C., or alternatively while cooling or heating.

A hydroxy group protected by a suitable acyl group, an organic silyl group or by optionally substituted 1-phenyl-lower alkyl is freed analogously to a correspondingly protected amino group. A hydroxy group protected by 2,2-dichloroacetyl is freed, for example, by basic hydrolysis, and a hydroxy group etherified by tert.-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Two hydroxy groups that are together protected by a preferably substituted methylene group, such as by lower alkylidene, for example isopropylidene, cycloalkylidene, for example cyclohexylidene, or benzylidene, can be freed by acid solvolysis, especially in the presence of a mineral acid or a strong organic acid.

Phosphoric acid lower alkyl esters, for example phosphoric acid methyl ester, are preferably cleaved by means of lithium bromide, but alternatively by alkaline hydrolysis. Phosphoric acid phenyl or benzl esters are preferably cleaved electrochemically, or alternatively by hydrogenolysis, it being possible to cleave benzyl esters, for example, in the presence of palladium catalysts, such as palladium-on-carbon, and phenyl esters, for example, in the presence of platinum or mixed platinum-palladium catalysts.

The processes described above, including the processes for removing protecting groups and the additional process steps are carried out in a manner known per se, for example in the presence or absence of solvents and diluents, if necessary in the presence of condensation agents or catalysts, at reduced or elevated temperature, for example in a temperature range of from approximately −20° C. to approximately 150° C., in a closed vessel and/or in an inert gas atmosphere, for example a nitrogen atmosphere.

Taking into account all the substituents in the molecule, there should be used, if necessary, for example if readily hydrolysable radicals are present, particularly mild reaction conditions, such as short reaction times, the use of mild acidic or basic agents in a low concentration, stoichiometric quantity ratios, and the choice of suitable catalysts, solvents, temperature and/or pressure conditions.

The invention also relates to those embodiments of the process in which a compound obtainable as intermediate at any stage of the process is used as starting material and the remaining process steps are carried out or the process is interrupted at any stage or a starting material is formed under the reaction conditions or is used in the form of a reactive derivative or salt. The starting materials used are preferably those which, according to the process, result in the compounds described above as being especially valuable.

The present invention also relates to novel starting materials and/or intermediates and to processes for their manufacture. The starting materials used and the reaction conditions chosen are preferably those which result in the compounds described in this Application as being especially preferred.

Mixtures of isomers can be separated into the individual isomers in a manner known per se, for example by fractional crystallisation, chromatography, etc., and racemates can be separated in a manner known per se into the optically active antipodes, for example with the formation of derivatives with optically active compounds and separation of the resulting diastereoisomeric mixtures.

The invention also relates to novel pharmaceutical preparations that contain as active ingredient, preferably as the only active ingredient, an amount of a compound of the formula I that is effective for the prophylaxis or treatment of virus infections, optionally together with pharmaceutically acceptable carriers that are suitable for enteral, for example oral or rectal, or parenteral administration and which may be inorganic or organic and solid or liquid. These preparations may be, for example, in dosage unit form. For example, there are used tablets or gelatine capsules that contain the active ingredient together with diluents, for example lactose, dextrose, sucrose, mannitol, sorbitol, cellulose and/or glycerine, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat or rice starch, gelatine, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colourings, flavourings and sweeteners. The pharmacologically active compounds of the present invention can also be used in the form of parenterally administrable preparations or in the form of infusion solutions. Such solutions are preferably isotonic aqueous solutions or suspensions, it being possible, for example in the case of lyophilised preparations that contain the active ingredient alone or together with a carrier, for example mannitol, for these to be manufactured before use. The pharmaceutical preparations may be sterilised and/or contain adjuncts, for example preservatives, stabilisers, wetting agents and/or emulsifiers, solubilisers, salts for regulating the osmotic pressure and/or buffers. The present pharmaceutical preparations which, if desired, may contain other pharmacologically active ingredients, such as antibiotics, are manufactured in a manner known per se, for example by means of conventional mixing, granulating, confectioning, dissolving or lyophilising processes, and contain approximately from 0.001% to 99%, especially from approximately 0.01% to approximately 10%, more especially from 0.1% to 5%, of the active ingredient(s), an active ingredient concentration of less than 1% being especially suitable for preparations that are to be applied topically.

The following are preferred as forms of administration to be applied topically: creams, ointments or pastes having an active ingredient content of from 0.001% to 1%, especially from 0.01% to 0.1%, for example 0.05%, for example ointments for intranasal application or lipsticks, or aqueous solutions having an active ingredient content of from 0.001% to 1%, especially from 0.05% to 0.5%, for example 0.1%, preferably isotonic, sterile and physiologically tolerable solutions, for example eye drops, preferably in microcontainers for once-only use, or sprays for use in the mouth and throat area.

The pharmaceutical preparations described in the Examples are especially suitable.

Creams are oil-in-water emulsions that contain more than 50% water. There are used as oily base especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. Suitable as emulsifier are surfaceactive substances having predominantly hydrophilic properties, such as corresponding non-ionic emulsifiers, for example fatty acid esters of polyalcohols or ethylene oxide adducts thereof, such as polyglycerine fatty acid esters or polyoxyethylene sorbitan fatty acid esters (Tweens), also polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are usually used in the presence of fatty alcohols, for example cetyl alcohol or stearyl alcohol. Additives to the aqueous phase are, inter alia, agents that reduce the drying-out of the creams, for example polyalcohols, such as glycerine, sorbitol, propylene glycol and/or polyethylene glycols, also preservatives, perfumes, etc.

Ointments are water-in-oil emulsions that contain up to 70%, but preferably from approximately 20% to approximately 50%, water or aqueous phase. Suitable as the fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerine, propylene glycol, sorbitol and/or polyethylene glycol, and also preservatives, perfumes, etc..

Fatty ointments are anhydrous and contain as base especially hydrocarbons, for example paraffin, petroleum jelly and/or liquid paraffins, also natural or partially synthetic fats, for example coconut fatty acid triglyceride, or preferably hardened oils, for example hydrogenated groundnut or castor oil, also fatty acid partial esters of glycerine, for example glycerine mono- and di-stearate, and also, for example, the fatty alcohols increasing the water-absorption capacity, emulsifiers and/or additives mentioned in connection with the ointments.

Pastes are creams and ointments having secretion-absorbing powder constituents, such as metal oxides, for example titanium oxide or zinc oxide, also talc and/or aluminium silicates, the purpose of which is to bind any moisture or secretions present.

Foams are administered from pressurised containers and are liquid oil-in-water emulsions in aerosol form; halogenated hydrocarbons, such as chlorofluoro-lower alkanes, for example dichlorodifluoromethane and dichlorotetrafluoroethane, are used as propellants. There are used as the oily phase, inter alia, hydrocarbons, for example paraffin oil, fatty alcohols, for example cetyl alcohol, fatty acid esters, for example isopropyl myristate, and/or other waxes. There are used as emulsifiers, inter alia, mixtures of emulsifiers having predominantly hydrophilic properties, such as polyoxyethylenesorbitan fatty acid esters (Tweens), and emulsifiers with predominantly lipophilic properties, such as sorbitan fatty acid esters (Spans). The customary additives, such as preservatives, etc., are also added.

Tinctures and solutions generally have an aqueousethanolic base to which are added, inter alia, polyalcohols, for example glycerine, glycols and/or polyethylene glycol, as humectants for reducing evaporation, and fat-restoring substances, such as fatty acid esters with lower polyethylene glycols, that is to say lipophilic substances that are soluble in the aqueous mixture, as a replacement for the fatty substances removed from the skin by the ethanol, and, if necessary, other adjuncts and additives.

The manufacture of the topically administrable pharmaceutical preparations is carried out in a manner known per se, for example by dissolving or suspending the active ingredient in the base or, if necessary, in a part thereof. When processing the active ingredient as a solution, it is generally dissolved in one of the two phases before emulsification; when processing the active ingredient as a suspension, it is mixed with part of the base after emulsification and then added to the rest of the formulation.

The invention relates especially to pharmaceutical preparations in dosage unit form for the prophylaxis or treatment of a virus infection in human beings, which preparations contain as the only active ingredient from 0.1 mg to 5 mg of a compound of the formula I together with a pharmaceutical carrier.

The following Examples illustrate the invention without limiting it in any way.

EXAMPLE 1

Under light narcosis with a mixture of equal parts of diethyl ether, ethanol and chloroform, groups of 30 female Tif:MF2f (SPF) mice or female BALB/c AnCbif Tif (SPF) mice having a body weight of 14–16 g are infected intranasally with lethal doses (approximately one LD80–90; 1–4 plaque forming units [PFU]) in the form of 0.05 ml portions each, of a suspension of Influenza A/Texas/1/77 (mouse-adapted strain) viruses.

At the point in time indicated below [days], based on the day of infection, the amounts mentioned in Table 4 of the individual active ingredients in 0.05 ml (intranasal administration) and 0.2 ml (oral administration) of a 0.005% by weight solution of the sodium salt of carboxymethylcellulose in twice-distilled pyrogen-free water, are administered once (single dose), in the manner indicated in Table 4, to 10 of these mice.

The remainder of the above-mentioned mice, that is to say 20, are used as a control, that is to say they receive a placebo (0.005% by weight solution of the sodium salt of carboxymethylcellulose).

The intranasal administration of the active ingredient is effected, under light narcosis, with a mixture of equal parts of diethyl ether, ethanol and chloroform.

Compound I=2-(1,2-dipalmitoyl-sn-glycero-3-hydroxyphosphoryloxy)-ethylamine;

Compound II=the sodium salt of 1-carboxy-2-(1,2-dioleoyl-sn-glycero-3-hydroxyphosphoryloxy)-ethylamine;

Compound III=2-(3-palmitoyl-rac-glycero-1-hydroxyphosphoryloxy)-ethylamine;

Compound IV = 2-(1-0-palmitoylpropanediol-3-0-hydroxyphosphoryloxy)-ethylamine;
Compound V = 2-(1,3-dipalmitoylglycero-2-hydroxyphosphoryloxy)-ethylamine.

TABLE 4

| Active ingredient | Method of administration | Time of administration [days] | Percentage of mice still alive 23 days after infection, as a function of the amount of active ingredient [mg/kg], statistical significance *P ≦ 0.05 **P ≦ 0.01 (Vierfelder-test) | | | | | 0 = control |
|---|---|---|---|---|---|---|---|---|
| | | | 10 | 1 | 0.1 | 0.01 | 0.001 | |
| I | oral | +7 | | 90** | 90** | 90** | | 30 |
| | oral | +7 | 90** | 90** | 100** | | | 30 |
| | intra-nasal | −7 | | 80** | 90** | 80* | | 20 |
| | intra-nasal | −7 | | | 50** | 70** | 70** | 5 |
| II | oral | +7 | | 100** | 80** | 100** | | 30 |
| | intra-nasal | −7 | | 40 | 50 | 80** | | 20 |
| III | intra-nasal | −7 | | | 60** | 70** | 50* | 5 |
| IV | oral | +7 | | | 10 | 30 | 40* | 0 |
| V | oral | +7 | | | | 80* | 40 | 25 |

EXAMPLE 2

4.5 g of the lithium salt of N-Boc-2-(1,3-dilauroyl-glycero-2-hydroxyphosphoryloxy)-ethylamine are dissolved in 50 ml of methylene chloride. 10 ml of trifluoroacetic acid are added to the solution at 0–5° C. and the whole is stirred for 2 hours at 10° C. to complete the reaction and finally completely concentrated by evaporation in vacuo. The residue is taken up in approximately 200 ml of a mixture of $CHCl_3:CH_3OH:H_2O = 1:1.2:1$. The aqueous phase is neutralised at 0–5° C. with approximately 10 ml of 2N sodium hydroxide solution (pH 5.0–5.5). The organic (lower) phase is separated off, concentrated to approximately half the volume and then 60 ml of acetone are added thereto at a bath temperature of 50° C. On cooling, 2-(1,3-dilauroylglycero-2-hydroxyphosphoryloxy)-ethylamine is precipitated in a form that can be readily filtered; m.p. 144–149° C., $R_f=0.51$ ($CHCl_3:CH_3OH:H_2O$:acetic acid = 15:5:1:0.1).

The starting material is obtained as follows:

Stage 2.1:

A solution of 6.85 g of 1,3-dilauroylglycerine in 50 ml of methylene chloride is added dropwise at −10° C. to a solution of 1.51 ml of phosphorus oxychloride and 3.1 ml of triethylamine in 25 ml of methylene chloride. The reaction mixture is stirred for 2 hours at 10° C. to complete the reaction, then cooled to 0° C. and, at this temperature, a solution of 2.5 ml of triethylamine and 2.9 g of N-Boc-ethanolamine in 10 ml of methylene chloride is added dropwise thereto. The reaction mixture is stirred for 1 hour at 30° C. to complete the reaction and then extracted with water, citric acid solution and sodium bicarbonate solution. The organic phase is concentrated by evaporation and the oily residue is chromatographed over silica gel with methylene chloride-ethyl acetate (5:1). N-Boc-2-(1,3-dilauroylglycero-2-methoxyphosphoryloxy)-ethylamine is obtained in the form of a colourless oil from the fraction having $R_f=0.40$.

Stage 2.2:

4.5 g of N-Boc-2-(1,3-dilauroylglycero-2-methoxyphosphoryloxy)-ethylamine are dissolved in 45 ml of acetone. 1.6 g of lithium bromide are added to the solution and the whole is heated under reflux for 2 hours. The solvent is then distilled off in vacuo and the residue is taken up in 90 ml of a mixture of chloroform-methanol-water (1:1.2:1). Two clear phases are formed. The organic (lower) phase is concentrated by evaporation and degassed under a high vacuum. The lithium salt of N-Boc-2-(1,3-dilauroyl-glycero-2-hydroxyphosphoryloxy)-ethylamine is obtained in the form of an oil which solidifies on being left to stand; $R_f=0.41$ ($CHCl_3:CH_3OH:NH_3$ [conc.] = 100:20:1).

EXAMPLE 3

Analogously to Example 2, there is obtained starting from capric acid 2-hydroxyethyl ester instead of 1,3-dilauroylglycerine (cf. Stage 2.1), 2-caprinoyl-oxyethyl-2-aminoethyl phosphate in the form of a white powder; m.p. 181–185° C., $R_f=0.17$ ($CHCl_3:CH_3OH:H_2O$:acetic acid = 15:5:1:0.1).

We claim:

1. Method for the prophylaxis and treatment of virus infections in warm-blooded animals, including human beings, characterized in that an effective dose of a cephalin derivative of the formula I

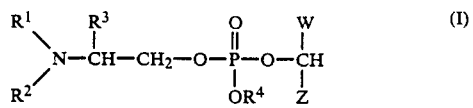

in which $R^1$ and $R^2$ each represents, independently of the other, hydrogen or lower alkyl, $R^3$ represents hydrogen, lower alkoxycarbonyl, carbamoyl or free or protected carboxy, $R^4$ represents hydrogen, lower alkyl, phenyl, 2-chlorophenyl, benzyl, 4-nitrobenzyl, 2,3,4,5,6-pentahdroxycyclohexyl, 2,3,4,5,6-pentaacetoxy-cyclohexyl, 2-aminoethyl, 2,3-dihydroxypropyl, trimethylisilyl or 2-hydroxy-3-glycycloxypropyl, W represents hydrogen and Z represents a 1,2-dihydroxyethyl, 2-hydroxyethyl or hydroxymethyl group in which at least one hydroxy group is esterfied by a C6? 30-alkanoic acid or etherified by an aliphatic C6? 30-alcohol and in which the other hydroxy group, if present, is free, esterified by a $C_{2-30}$-alkanoic acid or etherified by an aliphatic Cl? 30-alcohol, or W represents hydroxymethyl or a hydroxymethyl group that is esterified by a $C_{6-30}$-alkanoic acid or etherified by an aliphatic $C_{6-30}$-alcohol and Z represents a hydroxymethyl group that is esterified by a $C_{6-30}$-alkanoic acid or etherified by an aliphatic $C_{6-30}$-alcohol, or of a pharmaceutically acceptable salt of what compound is administered.

2. Method according to claim 1, characterized in that a compound of the formula I in which $R^1$ and $R^2$ each represents, independently of the other, hydrogen or $C_{1-2}$-alkyl, $R^3$ represents hydrogen, carboxy of benzyloxycarbonyl, $R^4$ represents hydrogen, W represents hydrogen and Z represents a 1,2-dihydroxyethyl or 2-hydroxyethyl group in each of which the 2-hydroxy group is esterified by a straight-chain alkanoic acid having 6, 10, 12, 14, 16, 18 or 20 carbon atoms or is etherified by a straight-chain alkanol having 6, 8, 16 or 18 carbon atoms and in which the 1-hydroxy group, if present, is free or esterified by a straight-chain alkanoic acid having 6, 10, 12, 14, 16, 18 or 20 carbon atoms or is etherified by a straight-chain alkanol having 1, 6, 8, 16 or 18 carbon atoms, or W represents hydroxymethyl or palmitoyloxymethyl and Z represents palmitoyloxymethyl, or a pharmaceutically acceptable salt thereof is administered.

3. Method according to claim 1, characterized in that a compound of the formula I in which $R^1$ and $R^2$ represent hydrogen, $R^3$ represents hydrogen or carboxy, $R^4$ represents hydrogen, W represents hydrogen and Z represents a 1,2-dihydroxyethyl group in which the 2-hydroxy group is esterified by a straight-chain $C_{14-18}$-alkanoic acid having an even number of carbon atoms or is etherified by a straight-chain alkanol having 16 or 18 carbon atoms, and in which the 1-hydroxy group is free or esterified by a straight-chain $C_{14-18}$-alkanoic acid having an even number of carbon atoms or is etherified by a straight-chain alkanol having 1, 16 or 18 carbon atoms, or a pharmaceutically acceptable salt thereof is administered.

4. Method according to claim 1 characterized in that a compound of the formula I in which W represents hydrogen and Z represents a 1,2-dihydroxyethyl group in which the 2-hydroxy group is esterified by a straight-chain $C_{14-18}$-alkanoic acid having an even number of carbon atoms and in which the 1-hydroxy group is either free or esterified by a straight-chain $C_{14-18}$-alkanoic acid having an even number of carbon atoms or a pharmaceutically acceptable salt thereof is administered.

5. Method according to claim 1 characterized in that a compound of the formula I in which W represents hydrogen and Z represents a 1,2-dihydroxyethyl group in which the two hydroxy groups are esterified by a straight-chain $C_{14-18}$-alkanoic acid having an even number of carbon atoms or W and Z each represent a hydroxymethyl group that is esterified by a straight-chain $C_{14-18}$-alkanoic acid having an even number of carbon atoms or a pharmaceutically acceptable salt thereof is administered.

6. Method according to claim 1 wherein a compound of the formula I in which $R^1$ and $R^2$ each represents, independently of the other, hydrogen or lower alkyl, $R^3$ represents hydrogen, carboxy or lower alkoxycarbonyl, $R^4$ represents hydrogen, and W and Z each represents hydroxymethyl esterified by a straight-chain $C_{6-22}$-alkanoic acid that is other than palmitic acid, or a pharmaceutically acceptable salt thereof is administered.

7. Method according to claim 1 wherein 2-(1,3-dilauroylglycero-2-hydroxyphosphoryloxy)-ethylamine is administered.

8. Method according to claim 1 characterized in that 2-(1,2-dipalmitoyl-sn-glycero-3-hydroxyphosphoryloxy)-ethylamine is administered.

9. Method according to claim 1 for the prophylaxis or treatment of infections caused by para-myxoviridae, ortho-myxoviridae, picornaviridae, chordopoxvirinae or alpha-herpesvirinae.

10. Method according to claim 1 for the prophylaxis or treatment of infections caused by para-influenza, Herpes simplex, encephalomyocarditis or vaccinia viruses.

11. Method according to claim 1 for the prophylaxis or treatment of infections caused by influenza viruses.

* * * * *